(12) United States Patent
Gray-Keller et al.

(10) Patent No.: US 7,390,813 B1
(45) Date of Patent: *Jun. 24, 2008

(54) PYRIDYLPIPERAZINES AND AMINONICOTINAMIDES AND THEIR USE AS THERAPEUTIC AGENTS

(75) Inventors: Mark P. Gray-Keller, Middleton, WI (US); Michael D. Winther, Vancouver (CA); Richard M. Fine, Ridgewood, NJ (US); Boris Klebansky, Demarest, NJ (US); Heinz Gschwend, Santa Rosa, CA (US); Daniel F. Harvey, San Diego, CA (US)

(73) Assignee: Xenon Pharmaceuticals Inc., Burnaby, BC (CA)

( * ) Notice: Subject to any disclaimer, the term of this patent is extended or adjusted under 35 U.S.C. 154(b) by 102 days.

This patent is subject to a terminal disclaimer.

(21) Appl. No.: 10/326,210

(22) Filed: Dec. 20, 2002

Related U.S. Application Data

(60) Provisional application No. 60/343,516, filed on Dec. 21, 2001, provisional application No. 60/394,506, filed on Jul. 9, 2002.

(51) Int. Cl.
A61K 31/495 (2006.01)
C07D 401/04 (2006.01)
(52) U.S. Cl. ......................... 514/255; 544/360
(58) Field of Classification Search .......... 514/255; 544/360
See application file for complete search history.

(56) References Cited

U.S. PATENT DOCUMENTS

| | | | |
|---|---|---|---|
| 2,985,657 A | 5/1961 | Janssen | |
| 3,975,384 A | 8/1976 | Narr et al. | |
| 4,439,606 A * | 3/1984 | Du et al. ................ | 544/356 |
| 5,166,147 A | 11/1992 | Earl | |
| 5,334,328 A | 8/1994 | Scherowsky et al. ... | 252/299.61 |
| 5,994,356 A | 11/1999 | Pieper et al. | |
| 6,372,746 B1 * | 4/2002 | Corbera-Arjona et al. ................ | 514/252.14 |
| 6,627,630 B1 | 9/2003 | Kawano et al. .......... | 514/248 |
| 6,677,452 B1 | 1/2004 | Chen et al. .............. | 544/365 |
| 6,911,447 B2 | 6/2005 | Mazur et al. | |
| 7,115,607 B2 * | 10/2006 | Fotsch et al. ........... | 514/252.13 |
| 2002/0045613 A1 | 4/2002 | Pauls et al. ............. | 514/210.18 |
| 2003/0157552 A1 | 8/2003 | Hayden et al. ............. | 435/7.1 |
| 2004/0082586 A1 | 4/2004 | Plant et al. ............. | 514/252.05 |
| 2004/0220171 A1 | 11/2004 | Pauls et al. ............. | 514/210.2 |
| 2005/0065143 A1 * | 3/2005 | Chakka et al. ............. | 514/218 |

FOREIGN PATENT DOCUMENTS

| | | |
|---|---|---|
| CA | 2114178 A1 | 7/1994 |
| DE | DT 23 41 295 A1 | 3/1975 |
| EP | 0 211 457 A2 | 2/1987 |
| EP | 320032 A1 | 6/1989 |
| EP | 0 156 433 B1 | 2/1991 |
| EP | 438230 A2 | 7/1991 |
| EP | 0 385 350 B1 | 11/1994 |
| EP | 1035115 A1 | 9/2000 |
| EP | 1156045 A1 | 11/2001 |
| EP | 1396487 A1 | 3/2004 |
| EP | 1452525 A1 | 9/2004 |
| JP | 10-7572 A | 1/1998 |
| WO | WO 88/07527 A1 | 10/1988 |
| WO | WO 88/08424 A1 | 11/1988 |
| WO | WO 97/26258 | 7/1997 |
| WO | WO 97/37975 A1 | 10/1997 |
| WO | WO 99/00386 | 1/1999 |
| WO | WO 99/47507 | 9/1999 |
| WO | WO 00/25768 | 5/2000 |
| WO | WO 00/44755 A1 | 8/2000 |
| WO | WO 01/25203 | 4/2001 |
| WO | WO 01/62954 | 8/2001 |
| WO | WO 01/68619 A1 | 9/2001 |
| WO | WO 01/81310 | 11/2001 |
| WO | WO 01/96327 A1 | 12/2001 |
| WO | WO 02/10154 | 2/2002 |
| WO | WO 02/26944 | 4/2002 |
| WO | WO 03/040125 | 5/2003 |
| WO | WO 03/043636 | 5/2003 |
| WO | WO 03/050088 | 6/2003 |
| WO | WO 03/066604 | 8/2003 |
| WO | WO 03/075929 | 9/2003 |
| WO | WO 03/076400 | 9/2003 |
| WO | WO 03/076401 | 9/2003 |
| WO | WO 03/076422 | 9/2003 |
| WO | WO 2004/010927 | 2/2004 |

OTHER PUBLICATIONS

"Trilateral project them:comparative study on reach through claims" Nov. 2001, p. 1.*

(Continued)

Primary Examiner—Celia Chang
(74) Attorney, Agent, or Firm—Seed IP Law Group PLLC

(57) ABSTRACT

Novel compounds useful in the treatment of, prevention of or protection against diseases and/or conditions related to metabolic syndrome and lipid metabolism, especially diseases of fatty acid and cholesterol metabolism, such as those mediated by stearoyl-CoA desaturase, are disclosed along with methods of employing said compounds for such uses.

8 Claims, 4 Drawing Sheets

OTHER PUBLICATIONS

Traveras et al. "Preparation of 3,4-disubstituted . . . " CA 137:325178 (2002).*
Kirkeby et al. 'Effects of prolonged . . . PMID:596247 (1977).*
Durrington et al. "The effect of a low cholesterol . . . " EMBASE No. 1978142387 (1977(.*
Ohashi S "Changes i cholesterol content . . . " BIOSIS No. 198069026634 (1980).*
Exhibit I, structureal delineation of CA143:7740 (2005).*
Attie, A. et al., "Relationship Between Stearoyl-CoA Desaturase Activity and Plasma Triglycerides in Human and Mouse Hypertriglyceridemia," *J Lipid Res.*, 43(11):1899-907, Nov. 2002.
Cohen, P. et al., "Role for Stearoyl-CoA Desaturase-1 in Leptin-mediated Weight Loss," *Science*, 297(5579):240-3, Jul. 12, 2002.
Ntambi, J.M. et al., "Loss of Stearoyl-CoA Desaturase-1 Function Protects Mice Against Adiposity," *Proc Natl Acad Sci U S A.*, 99(17):11482-6, Aug. 20, 2002.
Attie, A.D. et al., "Relationship between stearoyl-CoA desaturase activity and plasma triglycerides in human and mouse hypertriglyceridemia," *Journal of Lipid Research 43*: 1899-1907, 2002.
Cohen, P. et al., "Role of Stearoyl-CoA Desaturase-1 in Leptin-Mediated Weight Loss," *Science 297*: 240-243, Jul. 12, 2002.
De Anteuno, R.J. et al., "Relationship between mouse liver delta-9 desaturase activity and plasma lipids," *Lipids 28*(4): 285-290, Apr. 1993.
Jeffcoat, R. et al., "The regulation of desaturation and elongation of fatty acids in mammals," *New Comprehensive Biochemistry 7* (Fatty Acid Metab. Its Regul.):85-112, 1984.
Ntambi, J.M. et al., "Loss of stearoyl-CoA desaturase-1 function protects mice against adiposity," *Proc. Natl. Acad. Sci. USA 99*(17): 11482-11486, Aug. 20, 2002.
Machine Translation of Claims for published Japanese patent application JP 10-7572.
Miyazaki, M. et al., "The Biosynthesis of Hepatic Cholesterol Esters and Triglycerides Is Impaired in Mice with a Disruption of the Gene for Stearoyl-CoA Desaturase 1," *The Journal of Biological Chemistry 275*(39): 30132-30138, Sep. 29, 2000.
Miyazaki, M. et al., "A lipogenic diet in mice with a disruption of the stearoyl-CoA desaturase 1 gene reveals a stringent requirement of endogenous monounsaturated fatty acids for triglyceride synthesis," *Journal of Lipid Research 42*: 1018-1024, 2001.
Ntambi, J.M., "Regulation of stearoyl-CoA desaturase by polyunsaturated fatty acids and cholesterol," *Journal of Lipid Research 40*: 1549-1558, 1999.
Park, E.I. et al., "Lipid Level and Type Alter Stearoyl CoA Desaturase mRNA Abundance Differently in Mice with Distinct Susceptibilities to Diet-Influenced Diseases," *Journal of Nutrition 127*: 566-573, 1997.
Boes et al., "Preparation of N-benzyl-4-tolylnicotinamides and related compounds as neurokinin-1 receptor antagonists", Chemical Abstracts, Abstract No. 133:207811, 2000.
Boissier et al., "Synthesis and Pharmacological Study of New Piperazine Derivatives. I. Benzylpiperazines", Journal of Medical Chemistry 6: 541-544, Sep. 1963.
CAS Registry No. 362000-30-4, Oct. 14, 2001, "3-Pyridinecarboxamide, 6-[4-[(2,2-dichloro-1-methycyclopropyl)carbonyl]-1-piperazinyl]-N-[3-(methylthio)propyl]-(9CI)".
CAS Registry No. 504430-63-1, Apr. 24, 2003, "3-Pyridinecarboxamide, 6-[4-[(2,2-dichloro-1-methylcyclopropyl)carbonyl]-1-piperazinyl]-N-[3-(diethylamino)propyl]-(9CI)".
Chen et al., "Preparation of a combinatorial library of pyridine carboxamides and sulfonamides for various pharmaceutical uses", Chemical Abstracts, Abstract No. 134:295742, 2001.
Cheng et al., "Preparation of N-pyridyl heterocyclyl sulfonamides as 11beta-hydroxysteroid dehydrogenase type 1 modulators", Chemical Abstracts, Abstract No. 145:418953, 2006.
Derwent World Patents Index, English Abstract of DE 2341925 Mar. 6, 1975.
Gotor et al., "Fungal and Bacterial Regioselective Hydroxylation of Pyrimidine Heterocycles," Tetrahedron 53(18): 6421-6432, 1997.
Herron et al., "Preparation of pyrazinyl-, pyridazinyl-, pyrimidinyl-, and pyridinyl-hexahydrodiazepines and their use as factor Xa inhibitors", Chemical Abstracts, Abstract No. 136:151189, 2002.
Hori et al., "Studies on Antitumor-active 2,3-Dioxopiperazine Derivatives. III. Synthesis and Structure-Antitumor Activity Relationship of 1-(4-Aminobenzyl)-2,3-dioxopiperazine Derivatives", Chem. Pharm. Bull. 29(5): 1253-1266, 1981.
Iwata et al., "Preparation of 1- (6-phenylpyridine-2-carbonl)piperazine derivatives as phosphodiesterase (PDE) IV inhibitors", Chemical Abstracts, Abstract No. 138:55982, 2002.
Jacobsen et al., "2-(Aminomethyl)chromans That Inhibit Iron-Dependent Lipid Peroxidation and Protect against Central Nervous System Trauma and Ischemia", Journal of Medicinal Chemistry 35(23): 4464-4472, 1992.
Jacobsen et al., "Novel 21-Aminosteroids That Inhibit Iron-Dependent Lipid Peroxidation and Protect against Central Nervous System Trauma", Journal of Medicinal Chemistry 33(4): 1145-1151, 1990.
Kois et al., "Preparation of anilinopyrimidines as JNK pathway inhibitors", Chemical Abstracts, Abstract No. 137:33309, 2002.
Kurtz et al., "The Zucker Fatty Rat as a Genetic Model of Obesity and Hypertension", Hypertension 13(6, Part 2): 896-901, Jun. 1989.
Lee et al., "beta-Cell lipotoxicity in the pathogenesis of non-insulin-dependent diabetes mellitus of obese rats: Impairment in adipocyte-beta-cell relationships", Proc. Natl. Acad. Sci. USA 91: 10878-10882, Nov. 1994.
Ratouis et al., "Synthesis and Pharmacological Study of New Piperazine Derivatives. II. Phenethylpiperazines", Journal of Medicinal Chemistry 8: 104-107, Jan. 1965.
Steck et al., "Pyridazines. VII. Some 3-Dialkylaminopyridazines", Journal of Heterocyc. Chem. 11: 1077-1079, Dec. 1974.
Toldy et al., "Piperazinderivate I. 3,4,5-Trimethoxybenzoylderivate, Eine Neue Verbindungsgruppe mit Antiulzerogener Wirkung", Acta Chimica Academiae Scientiarum Hungaricae Tomus 49(3): 265-286, 1966.
Toldy et al., "Piperazine derivatives. II. Chlorobenzoxamine analogs", Chemical Abstracts, Database Accession No. 1967:473577, 1967.
Toldy et al., "Phenothiazine derivatives. VII. Preparation of selectively acting phenothiazine derivatives", Chemical Abstracts, Database Accession No. 1968:95776, 1968.
Thunus, "Synthesis and pharmacological properties of some 2,5-substituted isopropyl and hydroxyethylpiperazinylpyridines", Chemical Abstracts, Database Accession No. 1977:601475, 1977.
Truett et al., "Rat obesity gene fatty (fa) maps to chromosome 5: Evidence for homology with the mouse gene diabetes (db)", Proc. Natl. Acad. Sci USA 88: 7806-7809, Sep. 1991.
Zhang et al., "Down-regulation of the Expression of the Obese Gene by an Antidiabetic Thiazolidinedione in Zucker Diabetic Fatty Rats and db/db Mice", The Journal of Biological Chemistry 271(16): 9455-9459, Apr. 19, 1996.

* cited by examiner

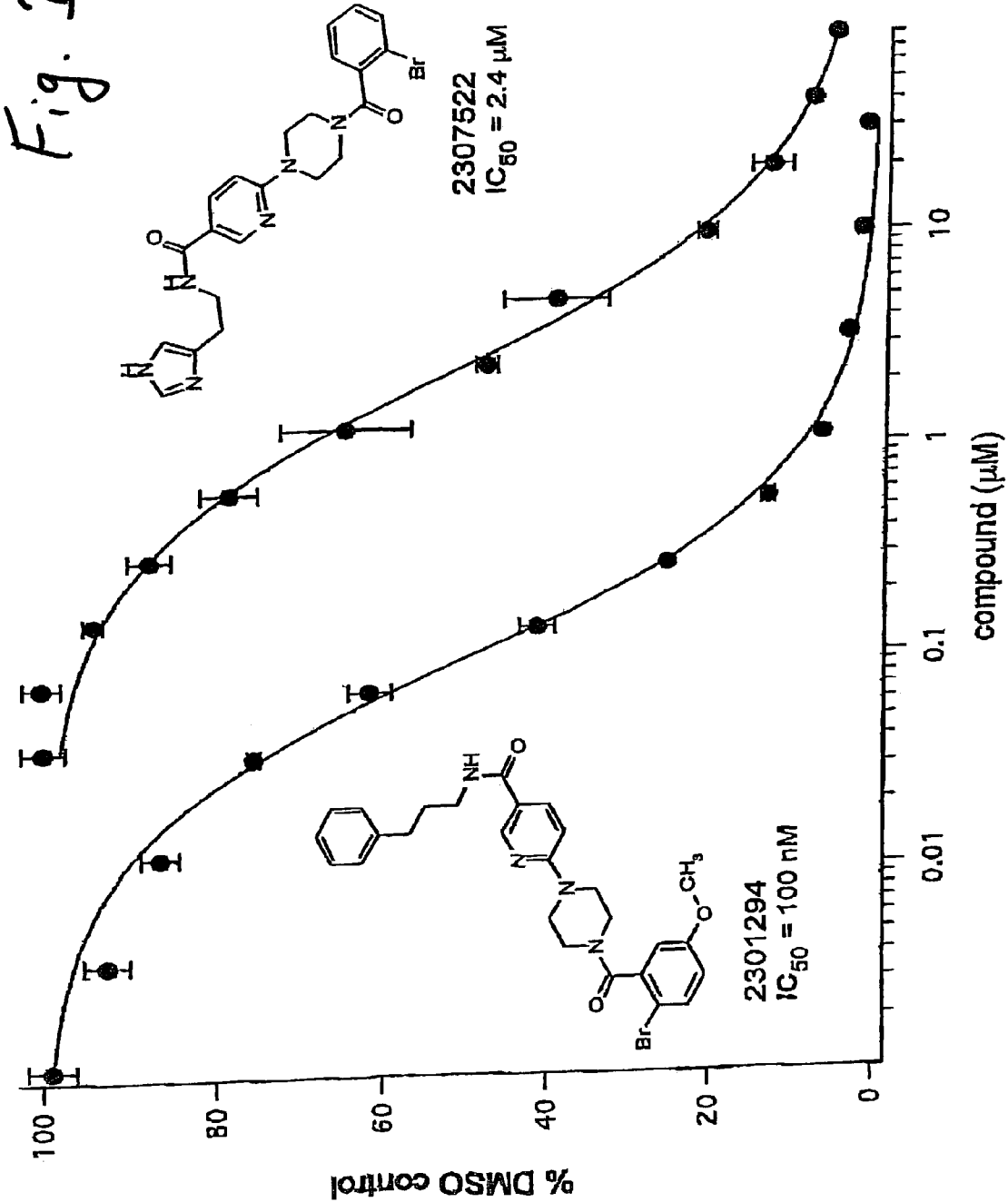

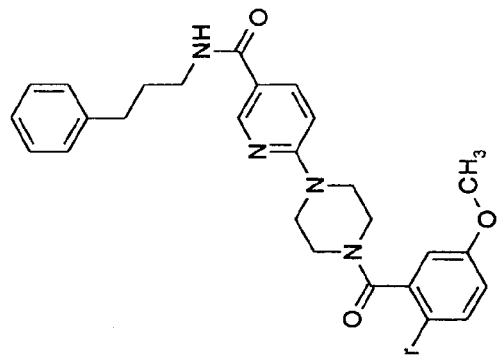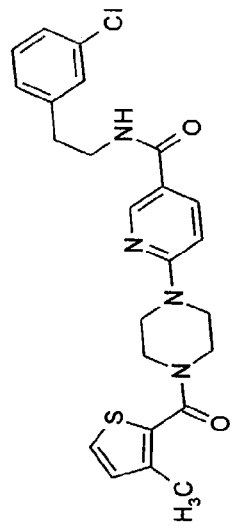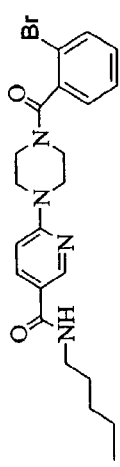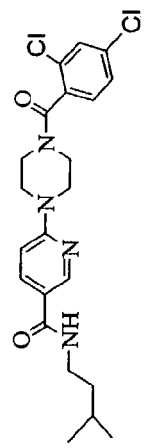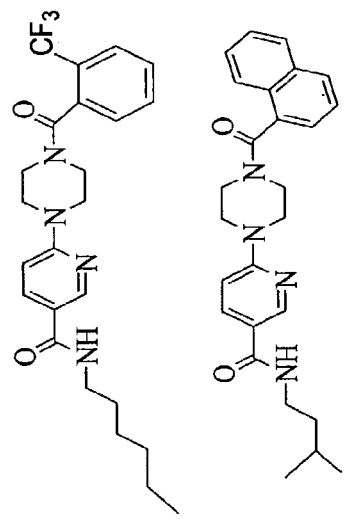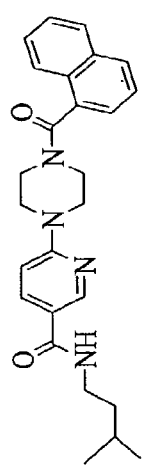
Fig. 2B

Fig. 2C
X19
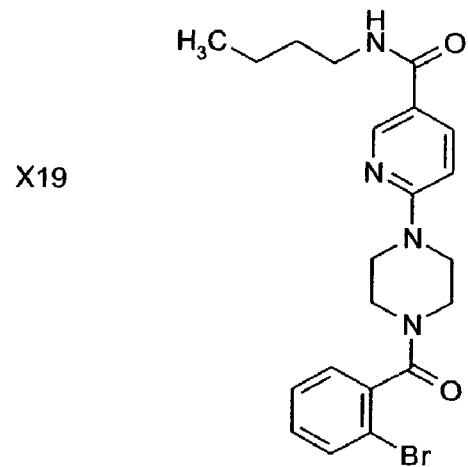
X20
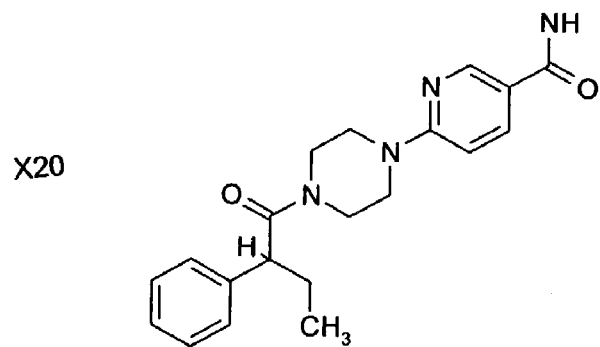
X21
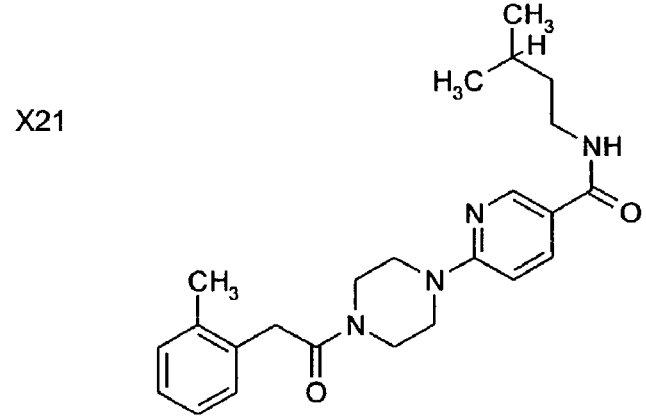

PYRIDYLPIPERAZINES AND AMINONICOTINAMIDES AND THEIR USE AS THERAPEUTIC AGENTS

This application claims the benefit of U.S. Provisional Application Ser. No. 60/343,516, filed 21 Dec. 2001, and 60/394,506, filed 9 Jul. 2002, the disclosures of which are hereby incorporated by reference in their entirety.

FIELD OF THE INVENTION

The present invention relates generally to the field of inhibitors of stearoyl-CoA desaturase and related enzymes, including pyridylpiperazines and aminonicotinamides, and the use of such compounds in treating and/or preventing various human diseases, including those mediated by stearoyl-CoA desaturase (SCD) enzymes, preferably SCD1, especially diseases related to elevated lipid levels, cardiovascular disease, diabetes, obesity, metabolic syndrome and the like.

BACKGROUND OF THE INVENTION

Acyl desaturase enzymes catalyze the formation of double bonds in fatty acids derived from either dietary sources or de novo synthesis in the liver. Mammals synthesize at least three fatty acid desaturases of differing chain length specificity that catalyze the addition of double bonds at the $\Delta 9$, $\Delta 6$, and $\Delta 5$ positions. Stearoyl-CoA desaturases (SCDs) introduce a double bond in the $\Delta 9$-position of saturated fatty acids. The preferred substrates are palmitoyl-CoA (16:0) and stearoyl-CoA (18:0), which are converted to palmitoleoyl-CoA (16:1) and oleoyl-CoA (18:1), respectively. The resulting monounsaturated fatty acids are substrates for incorporation into phospholipids, triglycerides, and cholesteryl esters.

A number of mammalian SCD genes have been cloned. For example, two genes have been cloned from rat (SCD1, SCD2) and four SCD genes have been isolated from mouse (SCD1, 2, 3, and 4). A single SCD gene, SCD1, has been characterized in humans. A second human SCD isoform has recently been identified, and because it bears little sequence homology to alternate mouse or rat isoforms it has been named human SCD5 or hSCD5. (See WO 02/26944 of Brownlie).

While the basic biochemical role of SCD has been known in rats and mice since the 1970's (Jeffcoat R. and James, A T. *Elsevier Science*, 4: 85-112 (1984); de Antueno, R J. *Lipids* 28(4)285-290 (1993)), it has only recently been directly implicated in human disease processes. Thus, an SCD1 enzyme highly useful in such studies has been identified and is further described in Brownlie et al, WO 01/62954 (30 Aug. 2001), the disclosure of which is hereby incorporated by reference in its entirety.

A number of mechanisms for the inhibition or modulation of SCD activity are available to suggest a means of approaching the rational design of SCD-modulating agents. Among these are the following, each of which serves to identify a specific mechanistic class of compound. One class of compounds includes those inhibitors that effectively inhibit SCD1 expression. This are believed to include putative PPAR agonists, such as thiazolidinedione compounds, and certain polyunsaturated fatty acids. A leading thiazolidinedione, troglitazone, has recently been withdrawn from human clinical use having been found to have an undesirable toxicity profile.

A second class of SCD inhibitors includes those inhibitors that effectively inhibit SCD1 enzymatic activity directly. Known examples include thia-fatty acids, cyclopropenoid fatty acids, and certain conjugated linoleic acid isomers. Specifically, Cis-12, trans-10 conjugated linoleic acid is known to effectively inhibit SCD enzyme activity and reduce the abundance of SCD1 mRNA while Cis-9, trans-11 conjugated linoleic acid does not. Cyclopropenoid fatty acids, such as those found in stercula and cotton seeds, are also known to inhibit SCD activity. For example, sterculic acid (8-(2-octyl-cyclopropenyl)octanoic acid) and Malvalic acid (7-(2-octyl-cyclopropenyl)heptanoic acid) are C18 and C16 derivatives of sterculoyl- and malvaloyl fatty acids, respectively, having cyclopropene rings at their $\Delta 9$ position. These agents inhibit SCD activity by inhibiting $\Delta 9$ desaturation. Other agents include thia-fatty acids, such as 9-thiastearic acid (also called 8-nonylthiooctanoic acid) and other fatty acids with a sulfoxy moiety.

Finally, the third class of inhibitors includes those agents that are capable of interfering with the proteins essential to the desaturase system, such as those agents that interfere with cytochrome $b_5$, NADH (P)-cytochrome $b_5$ reductase, and terminal cyanide-sensitive desaturase. This latter group of compounds may well be toxic and therefore of little use.

The known modulators of delta-9 desaturase activity are either not useful for treating the diseases and disorders linked to SCD1 biological activity as claimed in this invention, or else they are otherwise unsatisfactory therapeutic agents. The thia-fatty acids, conjugated linoleic acids and cyclopropene fatty acids (malvalic acid and sterculic acid) are neither useful at reasonable physiological doses, nor are they specific inhibitors of SCD1 biological activity, rather they demonstrate cross inhibition of other desaturases, in particular the delta-5 and delta-6 desaturases by the cyclopropene fatty acids. In some cases, it is preferred to identify compounds which inhibit SCD specifically and do not cross inhibit delta-5 desaturase and/or delta-6 desaturase.

Using such methodology, new classes of compounds have been identified and disclosed herein that are useful in modulating SCD activity and thereby regulating lipid levels, especially plasma lipid levels.

BRIEF SUMMARY OF THE INVENTION

In one aspect, the present invention provides agents that modulate the activity and/or expression of stearoyl-CoA desaturase 1 (SCD1), especially where said modulating ability was first determined using an assay comprising SCD1 biological activity or a gene encoding SCD1. Pharmaceutical compositions comprising such agents are specifically encompassed.

Thus, the present invention provides a method for treating a patient for, or protecting a patient from developing, an SCD-mediated disease or condition, comprising administering to a patient afflicted therewith, or at risk thereof, a therapeutically effective amount of a compound that modulates the activity of stearoyl-CoA desaturase (SCD).

In another aspect, the present invention provides pyridylpiperazine and aminonicotinamide compounds which are useful as therapeutic agents. Pharmaceutical compositions comprising such agents are specifically contemplated In a preferred embodiment, such therapeutic candidates are pyridylpiperazine derivatives, preferably those having a structure as described by Formula I. Other structures include the aminonicotinamide derivatives depicted in Formulas 2 and 3.

The present invention further relates to methods for treating a range of diseases involving lipid metabolism utilizing compounds identified by the methods disclosed herein. In accordance therewith, there is disclosed herein a range of compounds having said activity, based on a screening assay for identifying, from a library of test compounds, a therapeutic agent which modulates the biological activity of said stearoyl-CoA desaturase (SCD) and is useful in treating a human disorder or condition relating to serum levels of lipids, such as triglycerides, VLDL, HDL, LDL, and/or total cholesterol.

It is a still further object of the present invention to provide agents useful in treating, preventing and/or diagnosing a disease or condition relating to SCD biological activity such as the diseases encompassed by cardiovascular disorders and/or metabolic syndrome (including dyslipidemia, insulin resistance and obesity).

It is a yet further object of the present invention to provide methods of preventing or treating a disease or condition related to elevated lipid levels, such as plasma lipid levels, especially elevated triglyceride or cholesterol levels, in a patient afflicted with such elevated levels, comprising administering to said patient a therapeutically or prophylactically effective amount of a composition as disclosed herein.

The present invention also relates to novel pyridylpiperazines having therapeutic ability to reduce lipid levels in an animal, especially triglyceride and cholesterol levels. Thus, the present invention relates to a pyridylpiperazine having a structure as shown as Formula 2.

In one preferred embodiment, such pyridylpiperazine of has the structure of Formula I wherein n=2, m=1, $R_1$H, $R_2$=2-phenylethyl, R3=2-trifluormethylphenyl, and X=C and having an IC50 value of 48 nM.

In another such preferred embodiment, the pyridylpiperazine has the structure of Formula I wherein n=2, m=1, $R_1$=H, $R_2$=isopentyl, $R_3$=2-trifluormethylphenyl, and X=C and having an IC50 value of 32 nM.

In an addition such preferred embodiment, the pyridylpiperazine has the structure of Formula I wherein n=2, m=1, $R_1$=H, $R_2$=3-phenylpropyl $R_3$=2-trifluormethylphenyl, and X=C and showing substantial activity such that better than 99% of the activity is inhibited at only 10 μM concentration of the compound.

The present invention also relates to composition containing the novel compounds disclosed herein. In one embodiment, the present invention relates to a composition comprising a pyridylpiperazine as disclosed herein, especially where such compound is novel, suspended in a pharmaceutically acceptable carrier and in an amount effective to modulate triglyceride level when administered to an animal. In a preferred embodiment of such composition, the animal has an elevated lipid level, preferably triglyceride and or cholesterol level, before administration of said pyridylpiperazine and said pyridylpiperazine is present in an amount effective to reduce said lipid level, preferably a triglyceride and/or cholesterol level.

In highly preferred embodiments of such composition, the pyridylpiperazine is a pyridylpiperazine of Formula 2, especially those that reduce the enzyme activity in a microsomal assay to less than 1% at no more than 10 μM concentration of the pyridylpiperazine compound.

The results for selected individual compounds of the invention and/or which are useful in the methods of the invention are provided in Table 4.

BRIEF DESCRIPTION OF THE DRAWINGS

FIG. 1 shows dose response curves for two of the pyridylpiperazines of the invention. The compound at the left shows much greater inhibitory ability (with $IC_{50}$ of 100 nM) than the compound at the right (with $IC_{50}$ of 2.4 μM).

FIGS. 2A-2C show the structure of some pyridylpiperazines of Formula 1. Activity for each compound was measured as the % remaining SCD activity at the indicated concentration of test compound in Table 5 (using a mouse microsome assay) as well as $IC_{50}$ values for certain compounds. The compound identification numbers are the same as in Tables 4 and 5.

DETAILED DESCRIPTION OF THE INVENTION

Figure 2A:
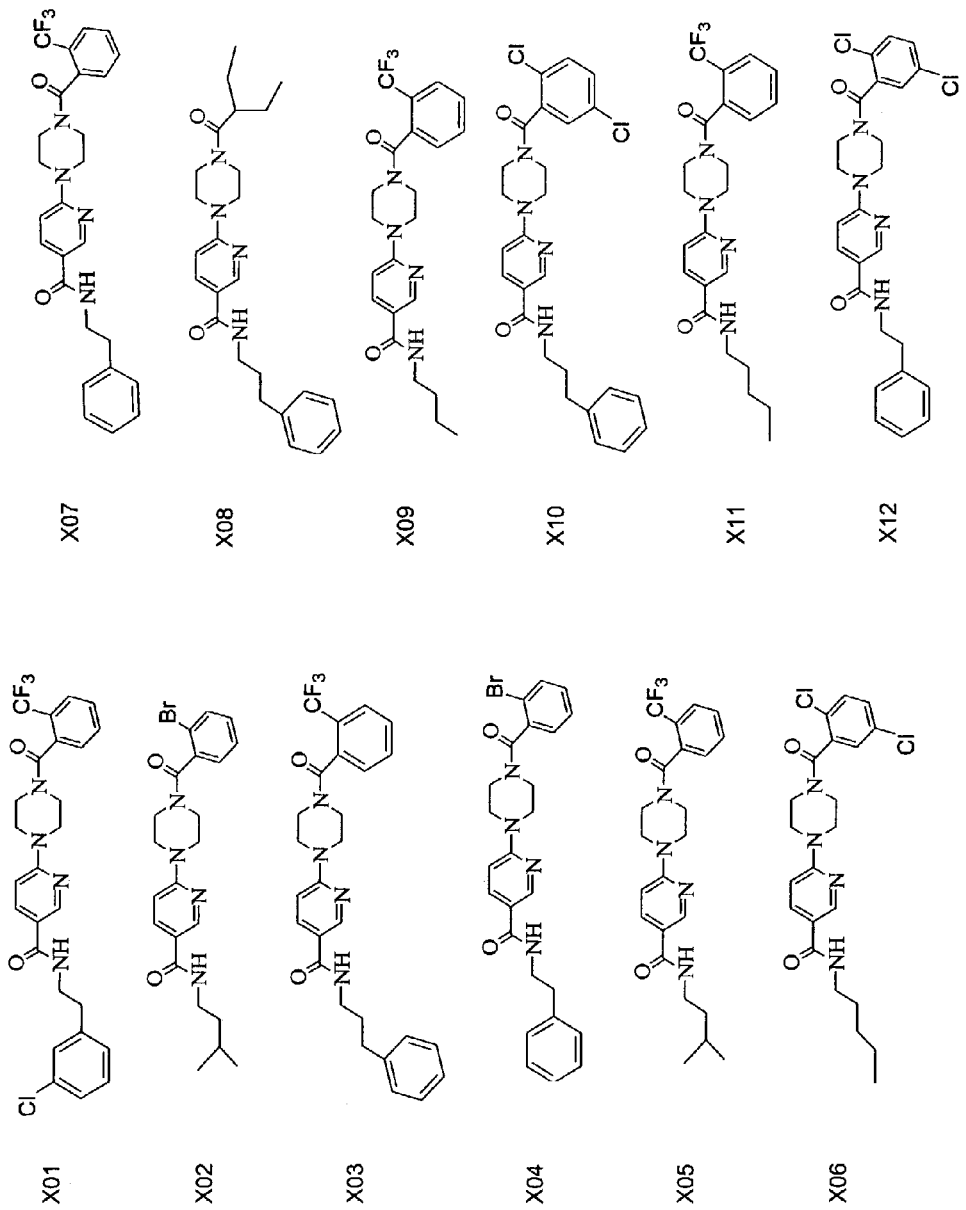

The present invention relates to compositions and methods for the treatment and/or prevention of diseases mediated by stearoyl-CoA desaturase enzymes (SCDs), especially human SCDs (hSCDs), preferably diseases of fatty acid and cholesterol metabolism, by administering to a patient in need of such treatment an effective amount of an SCD-modulating, especially inhibiting, agent as disclosed herein.

In general, the present invention provides a method for treating a patient for, or protecting a patient from developing, a lipid-related condition or disease, wherein lipid levels in an animal, especially a human being, are outside the normal range (i.e., abnormal lipid level, such as elevated plasma lipid levels), especially levels higher than normal, preferably where said lipid is a fatty acid, such as a free or complexed fatty acid, triglycerides, phospholipids, or cholesterol, such as where LDL-cholesterol levels are elevated or HDL-cholesterol levels are reduced, or any combination of these, where said lipid-related condition or disease is an SCD-mediated disease or condition, comprising administering to an animal, such as a mammal, especially a human patient, a therapeutically effective amount of a compound that modulates the activity of stearoyl-CoA desaturase (SCD), preferably human SCD1. In a preferred embodiment of such a method, the compounds disclosed herein are useful for the methods of the present invention. In addition, the methods of the invention can be used to find other compounds also useful in treatment.

In accordance therewith, the present invention provides chemical agents, in the form of small organic compounds, which include novel compounds, that modulate, preferably inhibit, the activity of human SCD enzymes, especially human SCD1 and methods for inhibiting this enzyme.

In one embodiment, the methods of the invention involve treatment of an animal, especially a human patient, afflicted with a disease, especially a disease related to elevated lipid levels, cardiovascular disease, diabetes, obesity, metabolic syndrome and the like, with a compound disclosed herein. In specific embodiments of such methods, the agents found useful according to the invention include chemical agents having a pyridylpiperazine core structure. The general formula is shown as Formula I:

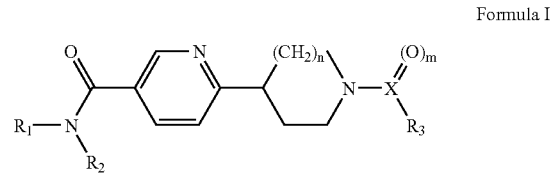

Formula I

Formula I shows the core structure of a pyridylpiperazine of the invention.

The general value of this class of compounds (Formula I) in modulating, especially inhibiting, the activity of lipid-metabolizing enzymes, especially SCD, most especially human SCD1, is demonstrated by the data of Table 4 and FIG. 2, wherein the ability of a number of such compounds to inhibit SCD biological activity is disclosed.

The pyridylpiperazine (or piperazinylpyridine) of Formula I includes structures wherein n=2 or 3 and m=1 or 2

$R_1$, $R_2$, and $R_3$ are each independently selected from H, lower alkyls,
straight or branched chain alkyl ($C_3$ to $C_{12}$),
straight or branched hydroxy-alkene ($C_3$ to $C_{12}$),
straight or branched chain ethers ($C_3$ to $C_{12}$),
straight or branched chain alkoxy or alkoxyalkyl ($C_3$ to $C_{12}$),
straight or branched aryl-alkyl or aryl-alkyl or
straight or branched heteroarylalkyl or alkylheteroaryl or
lower alkoxy alkene whereby aryl is selected from phenyl or substituted phenyls (mono-, di-, tri-substituted) especially where these substituents include F, Cl, Br, I, $CF_3$, OH, O-lower alkyl,
and R3 may also be phenyl, phenyl substituted with 1 to 6 groups (including F, Cl, Br, I, $CH_3$, $CF_3$, OH, OR', wherein R' is lower alkyl), aryl-alkylene, aryl-cycloalkyl, naphthyl, heteroaryl, or substituted heteroaryl, (such heteroaryl including especially thienyl, pyridyl, furyl, pyrrolyl, isoquinolyl, optionally substituted with 1 to 6 groups (including F, Cl, Br, I, $CH_3$, $CF_3$, OH, OR'', wherein R'' is lower alkyl)) or aryl-alkyl, such as benzyl (wherein the latter is optionally substituted with alkyl groups up to 12 carbons in length, preferably methyl, ethyl and propyl groups, and their derivatives) and/or where the benzyl comprises halogen substituents.

and wherein X=C, S, CNH, COR (and R is lower alkyl). In a preferred embodiment, the compounds of the invention include those alternative embodiments of Formula I set out in FIG. 2 and Tables 1 and 2.

In a preferred embodiment of any of the compounds of the invention, $R_1$ is hydrogen.

In another preferred embodiment, $R_2$ is a member selected from phenylpropyl (especially 3-phenylpropyl), isopentyl, n-pentyl, imidazole-propyl, especially 3-(N-imidazolyl)-propyl, n-butyl, 2-methyl-1-butyl, 2,4-dichlorophenyl, furyl, especially furylmethyl, 3-chlorophenylethyl, and 2-(4-imidazolyl)-methyl.

In other preferred embodiments, $R_2$ is a member selected from any of the groups shown in Table 1.

In another preferred embodiment, $R_3$ is a member selected from bromophenyl, preferably 2-bromophenyl, 3-butyl, 2-methylbenzyl, 2,4-dimethylphenyl, phenylethyl, preferably 1-(4-chlorophenyl)-ethyl, methylthienyl, preferably 5-methylthienyl, 1,4-dichlorophenyl, 2-bromophenyl, 1-phenylpropyl, 2-methyl-1-butyl, 2-phenylcyclopropyl, chloropyridyl, preferably 2-chloropyridyl, chlorophenylethyl, preferably 3-chlorophenylethyl, most preferably 2-(3-chlorophenyl)ethyl, nitrophenyl, preferably methylnitrophenyl, most preferably 5-methyl-2-nitrophenyl.

In other preferred embodiments, $R_3$ is a member selected from any of the groups shown in Table 2.

As used herein the term "aryl-alkyl" or "alkyl-aryl" refers to a substituent wherein an aromatic group is attached to an alkyl group and may include, for example, a benzyl-group or derivatives of a benzyl-group wherein substituents appear attached either to the ring (the aromatic portion of the aryl-alkyl group) or to the alkyl portion of the aryl-alkyl group. Where the aromatic ring portion of the aryl-alkyl or alkyl-aryl group contains an atom other than carbon, such as a nitrogen, sulfur or oxygen atom, the aryl-alkyl or alkyl-aryl is referred to as a heteroaryl-alkyl or alkyl-heteroaryl group, respectively. Again, substituents may be attached to the ring portion or the alkyl portion of the grouping. In addition, the alkyl portion may itself be a ring structure that is either saturated or partially unsaturated and may include, by non-limiting example, a cyclopropyl, cyclobutyl, cyclopentyl, cyclohexyl and the like, or any saturated or partially saturated aliphatic rings from 3 carbon atoms to as many as 12 carbon atoms in the ring. Unsaturated groups may also appear either in the aliphatic ring or attached to it. These may include such rings as, for example, cyclohexyl rings containing one or two double bonds.

In addition, the aromatic portion of the aryl-alkyl or heteroaryl-alkyl group may contain aromatic rings with varying numbers of atoms, including heteroaromatic rings wherein more than one non-carbon appears, and in which the non-carbon (or hetero) atoms are the same or different, such as rings with two nitrogens, rings with two oxygens, rings with two sulfurs, or rings with a sulfur and nitrogen, or a nitrogen and oxygen, or a sulfur and oxygen, and the like.

In addition, the aliphatic portion of such aryl-alkyl or alkyl-aryl groups may be attached to the core of the overal structure through either the aromatic or aliphatic portion of the substituent. Further, the aliphatic portion of the group may be a straight chain (such as ethyl, n-propyl, n-butyl, n-pentyl, n-hexyl, and the like) or a branched chain structure (such as isopropyl, isobutyl, isopentyl and the like). In addition, the straight or branched chain aliphatic portio of the aryl-alkyl or alkyl-aryl group may contain double and/or triple bonds or may comprise substituents that contain double and/or triple bonds.

In addition, the compounds of the present invention include the pyridine derivatives (or aminonicotinamide derivatives) having of the structure of Formula II (which shows the core structure for an aminonicotinamide class of compounds according to the invention).

Formula II

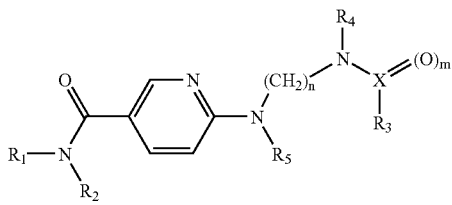

wherein n=2 or 3 and m=1 or 2

$R_1$ and $R_2$ are each independently selected from H, lower alkyl,
lower oxy-alkene or alkyloxy, straight or branched alkyl ($C_3$ to $C_{12}$),
straight or branched hydroxy-alkylene ($C_3$ to $C_{12}$),
straight or branched aryl-alkyl, especially benzyl, or
straight or branched heteroarylalkyl or
lower alkoxy aryl wherein aryl is selected from phenyl or substituted phenyls (mono-, di-, tri-substituted) especially where these are F, Cl, Br, I, $CF_3$, OH, O-lower alkyl, and $R_3$=phenyl, phenyl substituted with 1 to 3 groups, (including F, Cl, Br, I, $CF_3$, OH, $OR_2$,) aryl-alkyl, such as benzyl, aryl-alkene, aryl-cycloalkyl, naphthyl, heteroaryl (the latter including especially thienyl, pyridyl, furyl, pyrrolyl, and isoquinolyl)

X=C, S, CNH, CO R' (but R' is not H)

R4=H, lower alkyl, cycloalkyl, cycloalkyl-alkylene, hydroxy-lower alkyl, lower alkoxyalkyl R5=H, lower alkyl, cycloalkyl, cycloalkyl-alkylene, lower alkyloxy, lower hydroxyalkyl, and lower alkoxyalkyl In another such embodiment, compounds useful in the methods of the invention are those having the structure of Formula III (an aminonicotinamide):

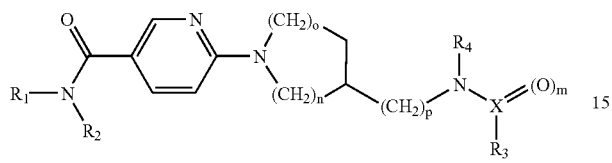

Formula III wherein n=0 to 3, m=1 or 2, o=0 to 3 and p=0 to 3

$R_1$=H, lower alkyls, HO-lower alkylene $R_2$=straight or branched alkyl ($C_3$ to $C_{12}$) or straight or branched hydroxy-alkylene ($C_3$ to $C_{12}$) or straight or branched aryl alkyl or straight or branched heteroarylalkyl or lower alkoxy alkylene whereby aryl is selected from phenyl or substituted phenyls (mono-, di-, tri-substituted) especially where these are I, $C_1$, $CF_3$, OH, O-lower alkyl, or $R_3$=phenyl, phenyl substituted with 1 to 3 groups, (including F, Cl, $CF_3$, OH, OR, wherein R is not H) aryl-alkylene, aryl-cycloalkyl, naphthyl, heteroaryl (the latter including especially thienyl, pyridyl, furyl, pyrrolyl, isoquinolyl)

$R_4$=H, lower alkyl, cycloalkyl, cycloalkyl-alkylene, hydroxy-lower alkyl, lower alkoxyalkyl X=C, S, CNH, COR, (but $R_1$ is not H)

In a preferred embodiment of the compounds of Formula 1, such as the structure

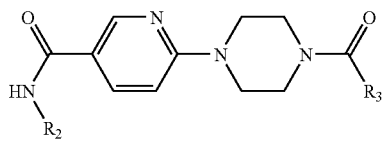

the compounds of the present invention comprise structures of Formula I wherein $R_1$ is H and X is C (as shown above). In other such preferred embodiments, $R_2$ is substituted by an amine-containing group selected from any of the groups of Table 1, most preferably one of those substituents that are boxed. These substituents are depicted as amine derivatives, wherein $R_2$ is shown attached to the amino group that represents the $NHR_2$ of the above structure. Thus, the $R_2$ groups for the above structure are shown as the groups attached to the amino $NH_2$— in the table.

R3 is selected from the groups of Table 2, which are shown as carboxylic acids for reaction to form the carbonyl portion of the above structure. Thus, the $R_3$ groups of the above structure are shown as the groups attached to the carboxyl —COOH in Table 2.

TABLE 1

Amine Building Blocks

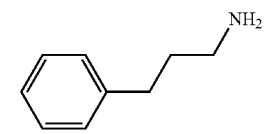

A1

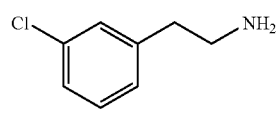

A2

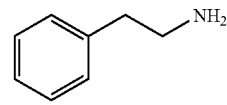

A6

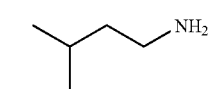

A9

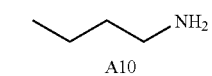

A10

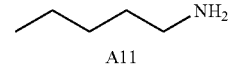

A11

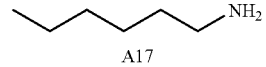

A17

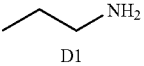

D1

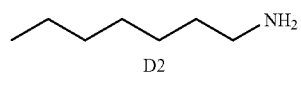

D2

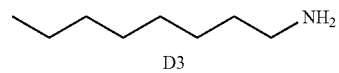

D3

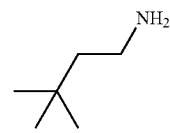

D4

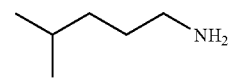

D5

TABLE 1-continued
Amine Building Blocks
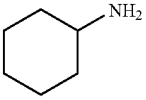
D6
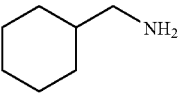
D7
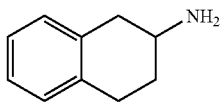
D8
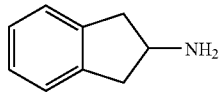
D9
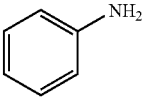
D10
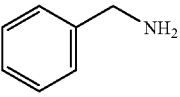
D11
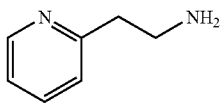
D12
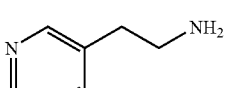
D13
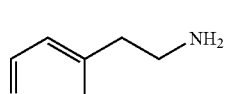
D14
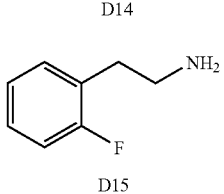
D15
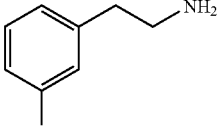
D16
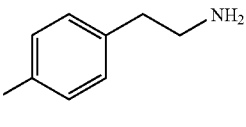
D17
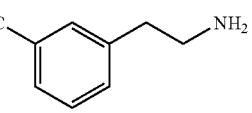
D18
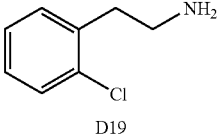
D19
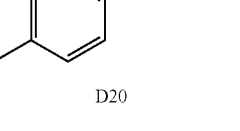
D20
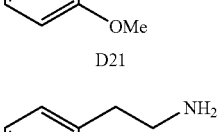
D21
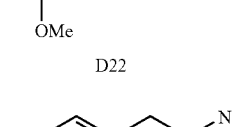
D22
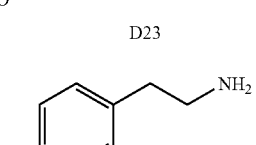
D23
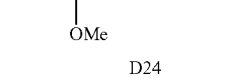
D24

TABLE 1-continued
Amine Building Blocks
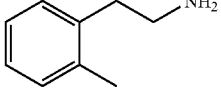
D25
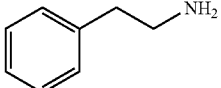
D26
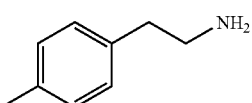
D27
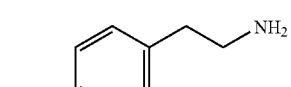
D28
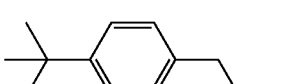
D29
D30
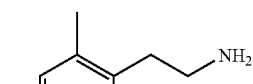
D31
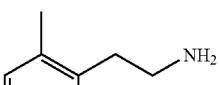
D32
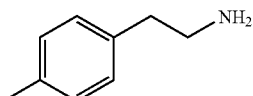
D33
TABLE 1-continued
Amine Building Blocks
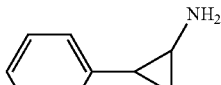
D34
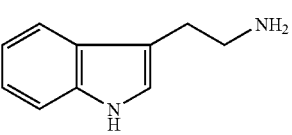
D35
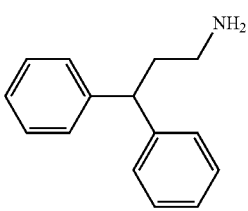
D36
In a further preferred embodiment, $R_3$ is substituted by a ring structure selected from any of the groups attached to the carboxyl in Table 2, most preferably one of those substituents that is boxed:
TABLE 2
Carboxylic Acid Building Blocks
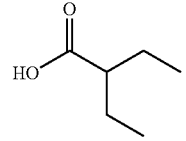
B9
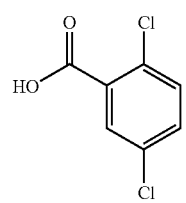
B14
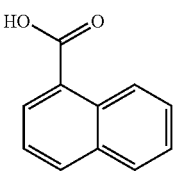
B18

TABLE 2-continued
Carboxylic Acid Building Blocks
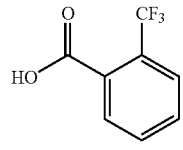
B25
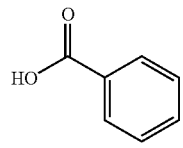
E1
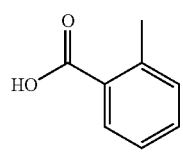
E2
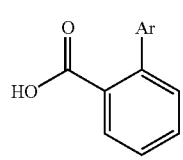
E3
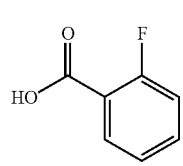
E4
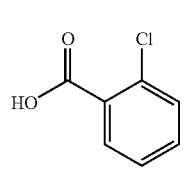
E5
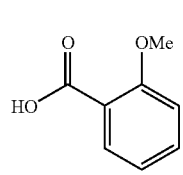
E6
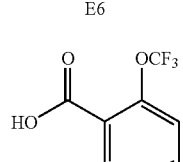
E7
TABLE 2-continued
Carboxylic Acid Building Blocks
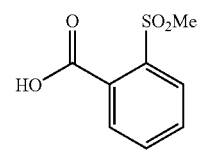
E8
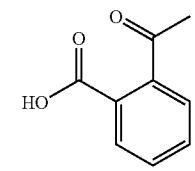
E9
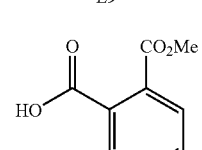
E10
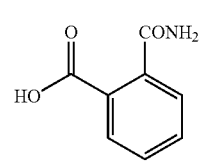
E11
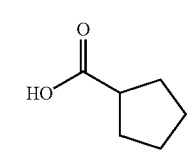
E12
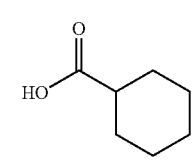
E13
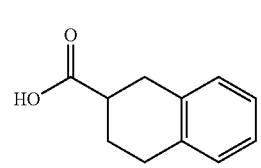
E14
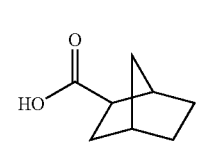
E15

TABLE 2-continued
Carboxylic Acid Building Blocks
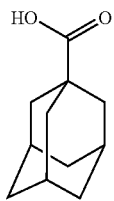
E16
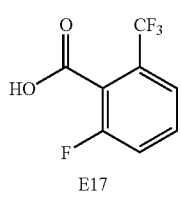
E17
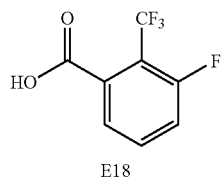
E18
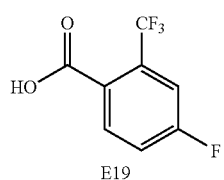
E19
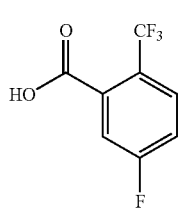
E20
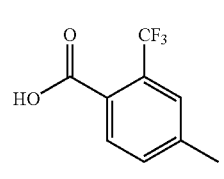
E21
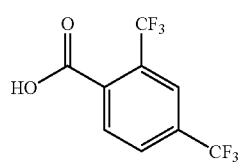
E22
TABLE 2-continued
Carboxylic Acid Building Blocks
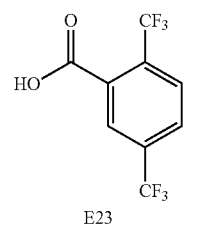
E23
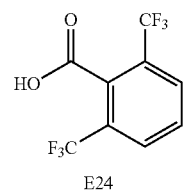
E24
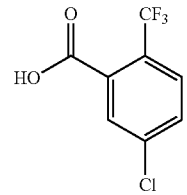
E25
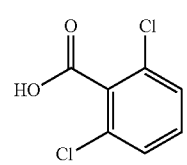
E26
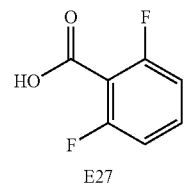
E27
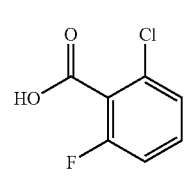
E28
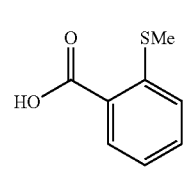
E29

TABLE 2-continued

Carboxylic Acid Building Blocks

E30

E31

In a most preferred embodiment, $R_2$ is a substituent selected from those of Table 1 and $R_3$ is a substituent selected from those of Table 3.

| Example No. | $R_3$—C(O)— | $R_2$ |
|---|---|---|
| 1 | 2-Br-5-OMe-benzoyl | phenylbutyl |
| 2 | 2-Br-benzoyl | ethoxybutyl |
| 3 | 2-CF3-benzoyl | isohexyl |
| 4 | 2,4-diMe-benzoyl | isohexyl |
| 5 | Et2CH-C(O)- | phenylbutyl |
| 6 | Et2CH-C(O)- | hexyl |

-continued

| Example No. | $R_3$—C(O)— | $R_2$ |
|---|---|---|
| 7 | 2-CF3-benzoyl | phenylbutyl |

Other preferred R2 and R3 groups are illustrated in Tables 1 and 2.

Synthetic Plan

In general, the compounds of the invention may be synthesized as follows:

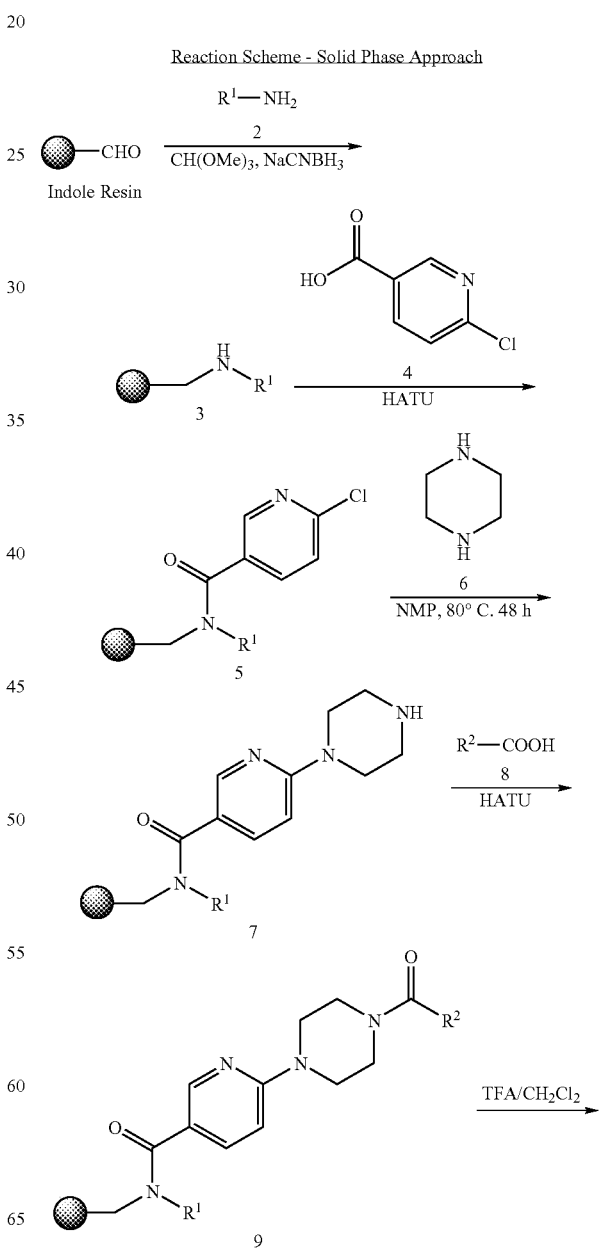

Reaction Scheme - Solid Phase Approach

-continued

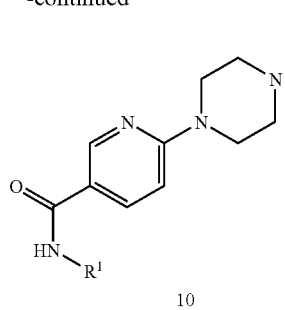
10

Experimental Procedures—Solid Phase Approach

A preferred synthetic scheme employs solid phase synthesis using Kan™ reactors. Kan™ reactors are rigid containers with mesh side walls. A single compound is synthesized in each one, and each one contains a unique, miniature radiofrequency label along with the actual solid phase resin.

Kan reactors are designed to be loaded with solid phase resin beads and an Rf tag. The synthesis takes place by allowing reagents to flow through the outer mesh walls of the Kan. Syntheses are performed using normal laboratory glassware and apparatus for heating, cooling, mixing, etc.

There are 3 sizes of Kan reactors available which may be used interchangeably with the AccuTag system—MicroKans, MiniKans, and MacroKans. Typically about 30-300 mg of most commercial resins are loaded into a Kan leaving enough space available for the resin to swell and still remain loose within the Kan.

Synthesis takes place by the flow of reagents through the mesh walls of the Kan. The Kan reactors permit virtually any synthetic chemistry which can be performed using loose solid phase resin and conventional laboratory glassware to be done using the AccuTag system.

The Kan is made of high-grade polypropylene with a polypropylene mesh side wall. The Kan is filled with the solid phase resin and the radiofrequency tag before being used in the synthesis. The appropriate Kan size can be selected from the table below.

Further information on the Irori Kan technology can be obtained from Discovery Partners, Inc., at www.discoverypartners.com.

All of the reagents, amines and carboxylic acids necessary to carry out the syntheses described below are commercially available from widely available sources.

Kans 1 (12 Kans) containing indole resin (90 mg per Kan, 0.9 mmol/g) were suspended in anhydrous trimethylorthoformate (40 mL). Amine 2 (comprising $R^1$, below) (10 mmol, 10 eq) was added, and the reaction was shaken at RT for 16 h. Sodium cyanoborohydride (1.3 g, 20 eq) was added and the reaction was shaken at RT for 1 h. Aqueous acetic acid (3.2 mL, 8% v/v) was slowly added and the reaction was shaken at RT for 3 h. The MiniKans 3 were washed alternately with MeOH and DCM for four cycles and dried under vacuum.

Kans containing 3 from seven reactions (total 84 MiniKans) were suspended in anhydrous DMF (250 mL). 6-Chloronicotinic acid (11.2 g, 10 eq), diisopropylethylamine (25 mL, 20 eq) and HATU (26.2 g, 10 eq) were added and the reaction was shaken at RT for 24 h. The Kans 5 were washed alternately with MeOH and DCM for four cycles and dried under vacuum.

The Kans containing 5 were suspended in anhydrous N-methylpyrrolidinone (250 mL). piperazine 6 (12.0 g, 20 eq) and diisopropylethylamine (49 mL, 40 eq) were added and the reaction mixture was heated at 80° C. for 48 h. The MiniKans containing 7 were washed alternately with MeOH and DCM for 4 cycles and dried under vacuum.

After sorting, Kans containing 7 (12 Kans) were suspended in anhydrous DMF (40 mL). Carboxylic acid 8 (comprising $R^2$ below) (10 mmol, 10 eq), diisopropylethylamine (3.5 mL, 20 eq) and HATU (3.8 g, 10 eq) were added and the reaction was shaken at RT for 24 h. The Kans containing 9 were then washed alternately with MeOH and DCM for five cycles and dried under vacuum.

Kans containing 9 (3 Kans) were treated with 20% TFA/DCM (9 mL) at RT for 2 h. Pyridylpiperazine 10 was obtained and purified by HPLC.

An alternative synthetic scheme includes a convergent solution-phase approach as summarized below. For example, the compound

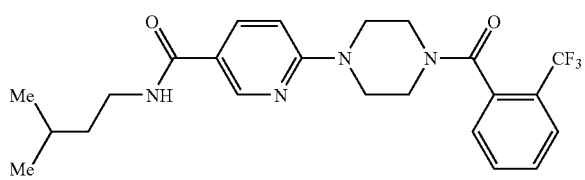

contains the core structure of Formula I wherein $R_1$ is H and $R_2$ is isopentyl, X=C, n=2, m=1 and $R_3$=2-trifluoromethylphenyl. This novel compound is a preferred embodiment of the present invention, including salts thereof, and is useful in the methods of the invention. This structure may be synthesized according to the following scheme:

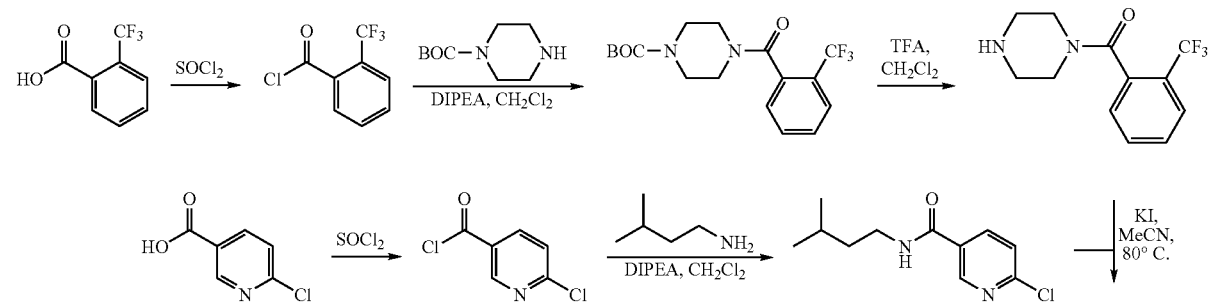

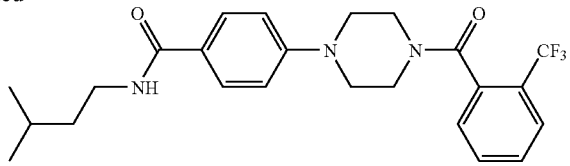

DPID08472885
IC50 = 32 nM

All reagents and reaction conditions employed in these syntheses are known to those skilled in the art and are available from ordinary commercial sources.

Therapeutic Uses of Compounds

This invention is directed to the compounds of the invention and their use in treating a disease, disorder or condition relating to levels of serum triglycerides, VLDL, HDL, LDL, total cholesterol and the like, cholesterol disorders, lipidemias or dyslipidemias, cardiovascular disease, diabetes, insulin resistance or decreased glucose tolerance, obesity, metabolic syndrome (including dyslipidemia, obesity and insulin resistance), Metabolic Syndrome X, coronary artery disease, atherosclerosis, heart disease, type II diabetes, ischemic stroke, transient ischemic attack (TIA), peripheral vascular disease, ischemic retinopathy, disorders characterized by defective reverse cholesterol transport, especially where the disease is a cardiovascular disease. In a preferred embodiment, the compounds of the invention will increase HDL levels in a patient and/or decrease triglyceride levels in a patient and/or decrease LDL levels in a patient. Either or all effects are directly associated with reduced risk of cardiovascular disease and coronary artery disease. Compounds of the invention may also be useful for treating hypertriglyceridemia, microalbuminemia, hyperuricaemia, hypercoagulability, metabolic syndrome and may also encompass any combination of these. Such conditions may be primary, such as primary hypertriglyceridemia, or they may be conditions which are secondary to another disorder or disease, such as hyperlipoproteinemias, familial histiocytic reticulosis, lipoprotein liapse deficiency, apolipoprotein deficiency (such as ApoCII deficiency or ApoE deficiency), erythrohepatic protoporphyria, a result of metal toxicity such as occurs in iron overload disorders, and the like, or they may be of unknown or unspecified etiology. As used herein, the term "metabolic syndrome" is a recognized clinical term and has been used to describe a condition comprising at least one of Type II diabetes, impaired glucose tolerance, and insulin resistance, together with at least two of the maladies hypertension, obesity, hypertriglyceridemia, low HDL, or microalbuminemia. Conditions exhibiting hyperuricaemia, hypercoagulability, hyperleptinaemia are not required for a diagnosis of metabolic disease but may still be part of the syndrome.

Compounds of the invention may also be used for weight reduction, to reduce body fat, for treatment of obesity, type I diabetes, type II diabetes, insulin resistance, glucose intolerance and as an insulin sensitizing agent. Additionally, compounds of the invention may be used to treat disorders of the skin, sebaceous gland and hair growth, including but not limited to skin cancer, hypertrichosis, hirsutism, acne, seborrhoeic dermaititis, atopic dermatitis, alopecia, baldness, disorders of pilosebaceous unit, meibomian cysts, and eccrine sweat glands, wound healing, keloid scar formation, and disorders relating to production of secretions from mucous membranes, monounsaturated fatty acids, and wax esters.

Compounds of the invention are also useful to treat diverse maladies as cancer and multiple sclerosis, hypertension, neurological diseases, eye diseases, and immune disorders. Compounds of the invention are also useful to prevent or treat viral infection. Compounds of the invention may be used to increase lean body mass or lean muscle mass, such as for enhancing performance in sports through muscle building. This latter indication emphasizes the potential for use of the compounds of the invention in animal husbandry, including for administration to bovine, porcine or avian domestic animals to reduce triglyceride production and provide leaner meat products and healthier animals.

Inhibitors of delta-9 desaturases, such as the compounds of the instant specification, are therefore useful for treating diseases and disorders in humans and other organisms, including all those human diseases and disorders which are the result of aberrant delta-9 desaturase biological activity or which may be ameliorated by modulation of delta-9 desaturase biological activity. Such diseases and disorders are sometimes referred to herein as "SCD-mediated."

The compounds identified in the instant specification inhibit the desaturation of various fatty acids (such as the C9-C10 desaturation of stearoyl-CoA) which is accomplished by delta-9 desaturases, such as stearoyl-CoA desaturase 1 (SCD1). As such these compounds inhibit the formation of various fatty acids such as triglycerides and downstream metabolites thereof. This may lead to an accumulation of stearoyl-CoA and other upstream precursors of various fatty acids; which may possibly result in a negative feedback loop causing an overall change in fatty acid metabolism. Any of these consequences may ultimately be responsible for the overall therapeutic benefit provided by these compounds.

Typically, a successful SCD1 inhibitory therapeutic agent will meet some or all of the following criteria. Oral availability should be at or above 20% (so that at least 20% is absorbed into the blood stream). Animal model efficacy should be less than about 2 mg/kg and the target human dose between 50 and 250 mg/70 kg, although doses outside of this range may be acceptable. The therapeutic index (or ratio of toxic dose to therapeutic dose) should be greater than 100. The potency (as expressed by $IC_{50}$ value) should be less than about 10 μM, preferably below about 1 μM and most preferably below about 50 nM. The agent may show reversible inhibition (i.e., competitive inhibition) and preferably does not inhibit other iron binding proteins. The selectivity of Δ9 inhibition over Δ5 or Δ6 should be greater than 100. The required dosage should be no more than about once or twice a day or at meal times.

A highly preferred compound of the invention has the structure of Formula I, wherein $R_1$ is H and $R_2$ is isopentyl, X=C, n=2, m=1 and $R_3$=2-trifluoromethylphenyl. This compound was shown to have lipid modulating activity in rats with evident stearoyl-CoA desaturase inhibitory activity. One study administered 9 doses (2 per day) to 4 rats at a dosage of 30 mg/kg body weight of the HCl salt of this compound and showed changes in fatty acid composition consistent with inhibition of SCD activity (including reduced formation of palmitoleic acid and reduced oleic acid with concomitant increased stearic acid levels).

Those skilled in the art know how to determine suitable doses of the compounds for use in treating the diseases and disorders contemplated herein. Therapeutic doses are generally identified through a dose ranging study in humans based on preliminary evidence derived from animal studies. Doses must be sufficient to result in a desired therapeutic benefit without causing unwanted side-effects for the patient.

Those skilled in the art are also familiar with determining administration methods (oral, intravenous, inhalation, subcutaneous, etc.), dosage forms, suitable pharmaceutical excipients and other matters relevant to the delivery of the compounds to a subject in need thereof.

Identification of the Compounds from a Compound Library

The identification of compounds of the invention was readily accomplished using the SCD enzyme and microsomal assay procedure described in Brownlie et al, supra.

Briefly, mouse or human liver microsomes (induced for SCD1 expression and containing cytochrome $b_5$ and cytochrome $b_5$ reductase) and NADH are suspended in buffer with a test compound, and reaction is initiated by addition of 0.025 mM tritiated stearoyl-CoA. This ligand is tritiated at the C9 and C10 position only. The reaction is allowed to proceed for between 5 and 20 minutes at room temperature, whereupon it is halted by addition of acid. Activated charcoal is then added, mixed, and centrifuged to separate labeled substrate from labeled water. An aliquot of supernatant is than tested for radioactivity using liquid scintillation counting. This is taken as a measure of delta-9 desaturase activity.

Confirming SCD Inhibitory Activity of Compounds of the Invention

Data showing inhibition of SCD by compounds of the invention are presented in Table 4. Table 4 sets forth the % remaining SCD activity at the indicated concentration of test compound in the indicated assay. Table 4 shows a broad range of pyridylpiperazines of Formula I that are potent inhibitors of SCD activity.

These results provide the basis for analysis of the structure-activity relationship (SAR) between test compounds and SCD. Certain R groups tend to provide more potent inhibitory compounds. SAR analysis is one of the tools those skilled in the art may now employ to identify preferred embodiments of the compounds of the invention for use as therapeutic agents.

Identifying the IC-50 of Compounds of the Invention

The IC-50 identified along with each compound described herein is a measure of the amount of compound required to achieve 50% inhibition of SCD activity, over a specific time period, in an SCD biological activity assay. Any process for measuring the activity of SCD enzymes, preferably mouse or human SCD enzymes, may be utilized to assay the activity of the compounds useful in the methods of the invention in inhibiting said SCD activity. Results of IC-50 measurements of various compounds of the invention are set out in FIGS. 1 and 2.

Other methods of testing the compounds disclosed herein are also readily available to those skilled in the art. Thus, in addition, said contacting may be accomplished in vivo. In one such embodiment, said contacting in step (a) is accomplished by administering said chemical agent to an animal afflicted with a triglyceride (TG)- or very low density lipoprotein (VLDL)-related disorder and subsequently detecting a change in plasma triglyceride level in said animal thereby identifying a therapeutic agent useful in treating a triglyceride (TG)- or very low density lipoprotein (VLDL)-related disorder. In such embodiment, the animal may be a human, such as a human patient afflicted with such a disorder and in need of treatment of said disorder.

In specific embodiments of such in vivo processes, said change in SCD1 activity in said animal is a decrease in activity, preferably wherein said SCD1 modulating agent does not substantially inhibit the biological activity of a delta-5 desaturase, delta-6 desaturase or fatty acid synthetase.

The model systems useful for compound evaluation may include, but are not limited to, the use of liver microsomes, such as from mice that have been maintained on a high carbohydrate diet, or from human donors, including persons suffering from obesity. Immortalized cell lines, such as HepG2 (from human liver), MCF-7 (from human breast cancer) and 3T3-L1 (from mouse adipocytes) may also be used. Primary cell lines, such as mouse primary hepatocytes, are also useful in testing the compounds of the invention. Where whole animals are used, mice used as a source of primary hepatocyte cells may also be used wherein the mice have been maintained on a high carbohydrate diet to increase SCD activity in mirocrosomes and/or to elevate plasma triglyceride levels (i.e., the 18:1/18:0 ratio); alternatively mice on a normal diet or mice with normal triglyceride levels may be used. Mouse models employing transgenic mice designed for hypertriglyceridemia are also available as is the mouse phenome database. Rabbits and hamsters are also useful as animal models, especially those expressing CETP (cholesteryl ester transfer protein).

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention also relates to compositions comprising the compounds of the invention suspended in a pharmacologically acceptable carrier. The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

A number of human diseases and disorders are the result of aberrant SCD1 biological activity and may be ameliorated by modulation of SCD1 biological activity using the therapeutic agents of the invention.

Inhibition of SCD expression may also affect the fatty acid composition of membrane phospholipids, as well as production or levels of triglycerides and cholesterol esters. The fatty acid composition of phospholipids ultimately determines membrane fluidity, while the effects on the composition of triglycerides and cholesterol esters can affect lipoprotein metabolism and adiposity.

Thus, in one aspect, the present invention relates to a method for treating a patient for an SCD-mediated disease, comprising administering to a patient afflicted therewith a therapeutically effective amount of a compound selected from the group consisting of the compounds of Formulas 1, 2 and 3.

In another aspect, the present invention relates to a method for protecting a patient against developing an SCD-mediated disease, comprising administering to a patient at risk thereof a therapeutically effective amount of a compound selected from the group consisting of pyridylpiperazines and aminonicotinamides. In preferred embodiments, such compounds have the structure of Formulas 1, 2 and 3.

The present invention also provides methods of treating a patient for, or preventing a subject from developing, a disease or condition mediated by SCD enzymes, where the treatment or prevention regimen comprises administering to a subject afflicted with such disease or condition, or at risk of developing such disease or condition, an effective amount of a compound disclosed herein. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians. Treatment or prevention of such conditions or syndromes are specifically contemplated by the present invention.

The present invention also relates to novel compounds, and compositions of such compounds, especially those in a form useful for treatment or prevention of any of the diseases, maladies or conditions described herein.

Thus, the present invention also relates to a pyridylpiperazine having a structure shown in FIG. 2. In a preferred embodiment thereof, the present invention encompasses a pyridylpiperazine of Formula I wherein
n=2, m=1,
$R_1$=hydrogen,
$R_2$=2-phenylethyl,
R3=2-trifluormethylphenyl, and
X=C.

In another such preferred embodiment, the compound is one having the structure of Formula I wherein
n=2, m=1,
$R_1$=hydrogen,
$R_2$=isopentyl,
R3=2-trifluormethylphenyl, and
X=C.

In an additional preferred embodiment thereof, the compound is one having the structure of Formula I wherein
n=2, m=1,
$R_1$=hydrogen,
$R_2$=3-phenylpropyl
R3=2-trifluormethylphenyl, and
X=C.

The present invention is also directed to compositions of such compounds, especially where such compounds are novel, and thus specifically contemplates a composition comprising a pyridylpiperazine as disclosed herein, preferably any of the pyridylpiperazines of FIG. 2 wherein such compound is suspended in a pharmaceutically acceptable carrier and in an amount effective to modulate lipid level when administered to an animal. In a preferred embodiment thereof, the lipid whose level is modulated is a triglyceride or cholesterol. In a highly preferred embodiment of such a composition, the animal has an elevated lipid level, especially an elevated triglyceride level and/or elevated cholesterol level, before administration of said pyridylpiperazine and said pyridylpiperazine is present in an amount effective to reduce said lipid level, especially said triglyceride level and/or said cholesterol level.

In a highly preferred embodiment of such compositions, the pyridylpiperazine is the pyridylpiperazine of Formula I wherein
n=2, m=1,
$R_1$=hydrogen,
$R_2$=2-phenylethyl,
R3=2-trifluormethylphenyl, and
X=C.

In another highly preferred embodiment of such compositions, the pyridylpiperazine is the pyridylpiperazine of Formula I wherein
n=2, m=1,
$R_1$=hydrogen,
$R_2$=isopentyl,
R3=2-trifluormethylphenyl, and
X=C.

In an additional highly preferred embodiment of such compositions, the pyridylpiperazine is the pyridylpiperazine of Formula I wherein
n=2, m=1,
$R_1$=hydrogen,
$R_2$=3-phenylpropyl
R3=2-trifluormethylphenyl, and
X=C.

The compounds and compositions of the invention were tested in mouse liver microsomes, 100 µg for 15 minutes at room temperature pre-incubation with the compound and 15 minutes at room temperature desaturation period. The results are summarized in Table 4, which shows percent remaining SCD activity as compared to a DMSO control in the mouse liver microsome assay at the indicated concentration of the test compound. Identification numbers are the same as those indicated in FIGS. 1 and 2 showing the structures and characteristics of the compounds.

The present invention also relates to a composition comprising a pyridylpiperazine, as disclosed hereinabove, wherein said pyridylpiperazine has the structure of Formula I and wherein
n=2 or 3 and m=1 or 2
$R_1$, $R_2$, and $R_3$ are each independently selected from H, lower alkyls,
straight or branched chain alkyl ($C_3$ to $C_{12}$),
straight or branched hydroxy-alkene ($C_3$ to $C_{12}$),
straight or branched chain ethers ($C_3$ to $C_{12}$),
straight or branched chain alkoxy or alkoxyalkyl ($C_3$ to $C_{12}$),
straight or branched aryl-alkyl or aryl-alkyl or
straight or branched heteroarylalkyl or alkylheteroaryl or
lower alkoxy alkene whereby aryl is selected from phenyl or substituted phenyls (mono-, di-, tri-substituted) especially where these substituents include F, Cl, Br, I, $CF_3$, OH, O-lower alkyl,
and $R_3$ may also be phenyl, phenyl substituted with 1 to 6 groups (including F, Cl, Br, I, $CH_3$, $CF_3$, OH, $OR_2$,), aryl-alkylene, aryl-cycloalkyl, naphthyl, heteroaryl, or substituted heteroaryl, (such heteroaryl including especially thienyl, pyridyl, furyl, pyrrolyl, isoquinolyl, optionally substituted with 1 to 6 groups (including F, Cl, Br, I, $CH_3$, $CF_3$, OH, $OR_2$)) or aryl-alkyl, such as benzyl (wherein the latter is optionally substituted with alkyl groups up to 12 carbons in length, preferably methyl, ethyl and propyl groups, and their derivatives) and/or where the benzyl comprises halogen substituents. and wherein X=C, S, CNH, COR (but R is not H).

suspended in a pharmaceutically acceptable carrier in an amount effective to modulate triglyceride level when administered to an animal.

In a preferred embodiment of such composition, X=C, R=H, m=1 and n=2.

In a highly preferred embodiment thereof, $R_2$ is a member selected from phenylpropyl (especially 3-phenylpropyl), isopentyl, n-pentyl, imidazole-propyl, especially 3-(N-imidazolyl)-propyl, n-butyl, 2-methyl-1-butyl, 2,4-dichlorophenyl, furyl, especially furylmethyl, 3-chlorophenylethyl, and 2-(4-imidazolyl)-methyl.

In another highly preferred embodiment thereof, $R_3$ is a member selected from bromophenyl, preferably 2-bromophenyl, 3-butyl, 2-methylbenzyl, 2,4-dimethylphenyl, phenylethyl, preferably 1-(4-chlorophenyl)-ethyl, methylthienyl, preferably 5-methylthienyl, 1,4-dichlorophenyl, 2-bromophenyl, 1-phenylpropyl, 2-methyl-1-butyl, 2-phenylcyclopropyl, chloropyridyl, preferably 2-chloropyridyl, chlorophenylethyl, preferably 3-chlorophenylethyl, most preferably 2-(3-chlorophenyl)ethyl, nitrophenyl, preferably methylnitrophenyl, most preferably 5-methyl-2-nitrophenyl.

In an especially preferred embodiment thereof, $R_2$ is a member selected from phenylpropyl (especially 3-phenylpropyl), isopentyl, n-pentyl, imidazole-propyl, especially 3-(N-imidazolyl)-propyl, n-butyl, 2-methyl-1-butyl, 2,4-dichlorophenyl, furyl, especially furylmethyl, 3-chlorophenylethyl, and 2-(4-imidazolyl)-methyl and $R_3$ is a member selected from bromophenyl, preferably 2-bromophenyl, 3-butyl, 2-methylbenzyl, 2,4-dimethylphenyl, phenylethyl, preferably 1-(4-chlorophenyl)-ethyl, methylthienyl, preferably 5-methylthienyl, 1,4-dichlorophenyl, 2-bromophenyl, 1-phenylpropyl, 2-methyl-1-butyl, 2-phenylcyclopropyl, chloropyridyl, preferably 2-chloropyridyl, chlorophenylethyl, preferably 3-chlorophenylethyl, most preferably 2-(3-chlorophenyl)ethyl, nitrophenyl, preferably methylnitrophenyl, most preferably 5-methyl-2-nitrophenyl.

The present invention also relates to a composition comprising a pyridylpiperazine wherein X=C, $R_1$ is hydrogen, m=1 and n=2. In a preferred embodiment of such composition, the pyridylpiperazine is one wherein $R_2$ is a member selected from any of the groups shown in Table 1. In another preferred embodiment of such composition, the pyridylpiperazine is one wherein $R_3$ is a member selected from any of the groups shown in Table 2. In a highly preferred embodiment of such composition, the pyridylpiperazine is one wherein $R_2$ is a member selected from any of the groups shown in Table 1 and $R_3$ is a member selected from any of the groups shown in Table 2.

TABLE 4

| ID Number | 10 uM average | s.d. | 1 uM average | s.d. | 0.1 uM average | s.d. |
|---|---|---|---|---|---|---|
| X01 | 1.42 | 1.33 | 9.05 | 0.32 | 57.77 | 2.33 |
| X02 | 1.27 | 0.49 | 5.49 | 0.34 | 25.68 | 3.11 |

TABLE 4-continued

| | 10 uM average | s.d. | 1 uM average | s.d. | 0.1 uM average | s.d. |
|---|---|---|---|---|---|---|
| X03 | 0.72 | 0.46 | 2.17 | 0.45 | 26.04 | 1.19 |
| X04 | 1.29 | 0.75 | 5.48 | 0.67 | 36.54 | 1.19 |
| X05 | 0.81 | 0.04 | 3.05 | 0.21 | 17.09 | 1.25 |
| X06 | 1.97 | 0.92 | 5.38 | 0.26 | 38.00 | 5.81 |
| X07 | 0.69 | 0.47 | 2.50 | 0.30 | 22.81 | 0.60 |
| X08 | 3.24 | 0.26 | 17.69 | 0.28 | 73.14 | 3.79 |
| X09 | 2.69 | 0.57 | 14.80 | 0.73 | 63.58 | 4.12 |
| X10 | 1.07 | 0.11 | 3.37 | 0.25 | 29.72 | 1.60 |
| X11 | 1.72 | 0.44 | 3.67 | 0.20 | 25.41 | 2.67 |
| X12 | 1.15 | 0.50 | 3.91 | 0.19 | 29.87 | 1.53 |
| X13 | 1.75 | 0.42 | 7.77 | 1.05 | 44.42 | 7.51 |
| X14 | 1.39 | 0.47 | 7.44 | 0.47 | 38.24 | 1.36 |
| X15 | 1.22 | 0.55 | 6.46 | 0.25 | 44.95 | 4.77 |
| X16 | 2.06 | 0.95 | 7.01 | 0.25 | 31.35 | 2.24 |
| Z' = | 0.85 | | 0.97 | | 0.85 | |

| | 10 uM average | s.d. | 1 uM average | s.d. | 0.1 uM average | s.d. |
|---|---|---|---|---|---|---|
| X17 | 1.01 | 0.23 | 10.59 | 0.43 | 61.74 | 7.23 |
| X18 | 3.41 | 0.61 | 32.64 | 0.72 | 86.33 | 3.08 |
| X19 | 3.57 | 0.29 | 18.59 | 0.66 | 75.14 | 2.35 |
| X20 | 1.84 | 0.30 | 12.23 | 0.17 | 57.22 | 2.38 |
| X21 | 3.94 | 0.96 | 33.28 | 1.29 | 74.82 | 3.27 |
| Z' = | 0.88 | | 0.92 | | 0.66 | |

% Remaining SCD activity compared to DMSO control in mouse liver microsome assay at concentration of test compound indicated. Compounds tested in mouse liver microsomes, 100 μg, 15 min RT preincubation with compound, 15 min RT desaturation period, Large volume benchtop tube method.

Such compositions are especially useful when the pyridylpiperazine is present in an amount effective to reduce a lipid level in an animal optionally in an animal having an elevated lipid level, preferably where the lipid is a triglyceride or cholesterol. Such compositions are also highly useful where the pyridylpiperazine is suspended in a pharmaceutically acceptable carrier and in an amount effective to modulate HDL-cholesterol level when administered to an animal.

TABLE 5

SCD Inhibitory Activity and $IC_{50}$ Values for Compounds of FIG. 2.

| Compound | % Activity 10 μM | % Activity 1 μM | % Activity 0.1 μM | $IC_{50}$ (nM) | Mol. Weight |
|---|---|---|---|---|---|
| X01 | 1.4 | 9.1 | 58 | | 516.15 |
| X02 | 1.3 | 5.5 | 26 | | 458.13 |
| X03 | 0.7 | 2.2 | 26 | | 496.21 |
| X04 | 1.3 | 5.5 | 37 | | 492.12 |
| X05 | 0.8 | 3.1 | 17 | 32 | 448.21 |
| X06 | 2 | 5.4 | 38 | | 448.14 |
| X07 | 0.7 | 2.5 | 23 | 48 | 482.19 |
| X08 | 3.2 | 18 | 73 | | 442.27 |
| X09 | 2.7 | 15 | 64 | | 434.19 |
| X10 | 1.1 | 3.4 | 30 | | 496.14 |
| X11 | 1.7 | 3.7 | 25 | 37 | 448.21 |
| X12 | 1.2 | 3.9 | 30 | | 482.13 |
| X13 | 1.8 | 7.8 | 44 | | 458.13 |
| X14 | 1.4 | 7.4 | 38 | | 448.14 |
| X15 | 1.2 | 6.5 | 45 | | 462.22 |
| X16 | 2.1 | 7 | 31 | | 430.24 |
| X17 | 1.01 | | | | 537.5 |
| X18 | 3.41 | | | | 469 |
| X19 | 3.57 | | | | 445.4 |
| X20 | 1.84 | | | | 470.6 |
| X21 | 3.94 | | | | 408.5 |

What is claimed is:
1. A method for lowering triglyceride serum levels in an animal, comprising administering to the animal a therapeutically effective amount of a compound selected from the group consisting of:
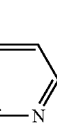

2. The method of claim 1 wherein the animal is a human.
3. A method for lowering LDL serum levels in an animal, comprising administering to the animal a therapeutically effective amount of a compound selected from the group consisting of:
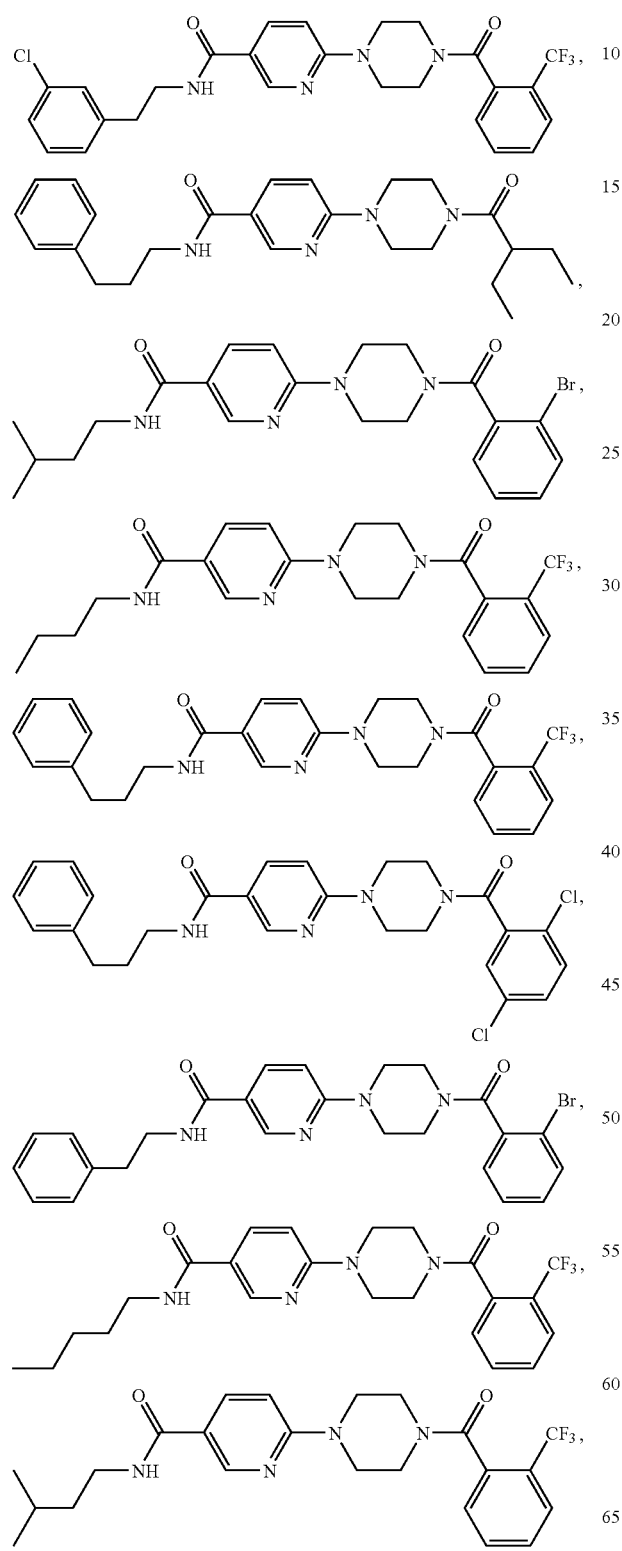
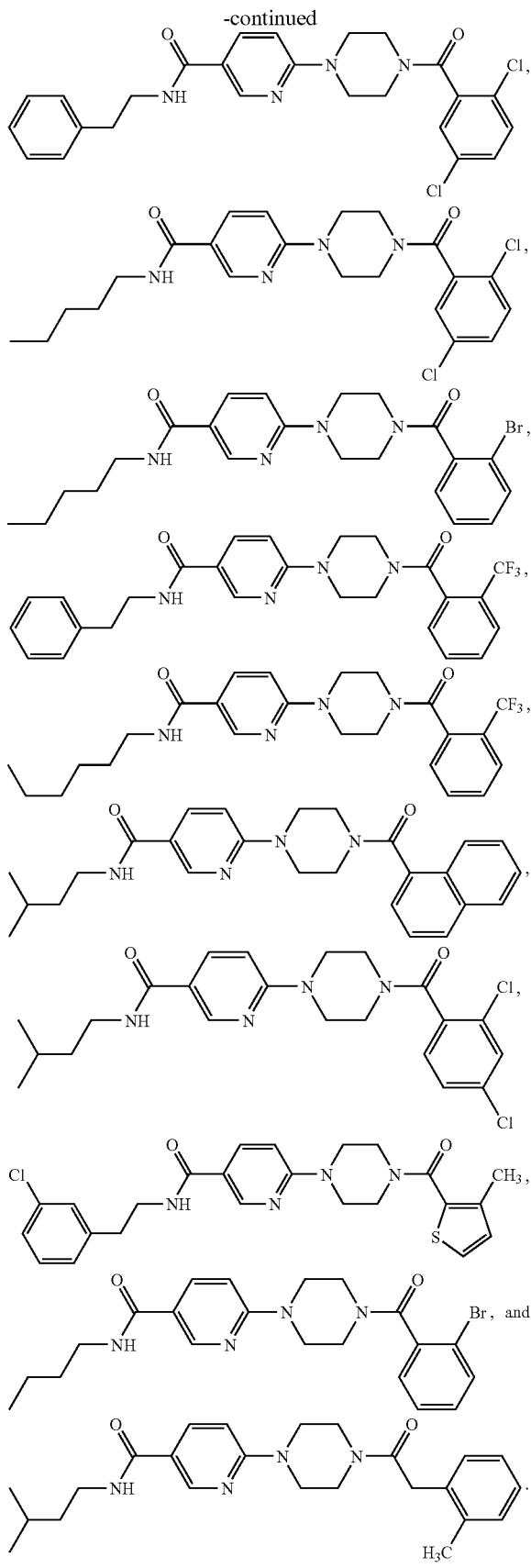

4. The method of claim 3 wherein the animal is a human.
5. A method for lowering VLDL serum levels in an animal, comprising administering to the animal a therapeutically effective amount of a compound selected from the group consisting of:
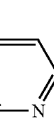

6. The method of claim 5 wherein the animal is a human.
7. A method for treating dyslipidemia in an animal, comprising administering to the animal a therapeutically effective amount of a compound selected from the group consisting of:
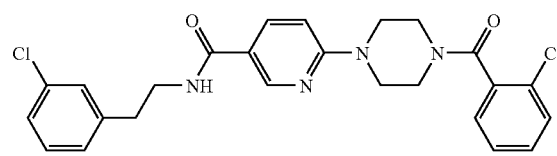
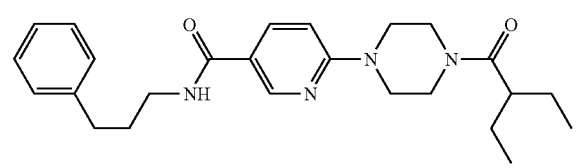
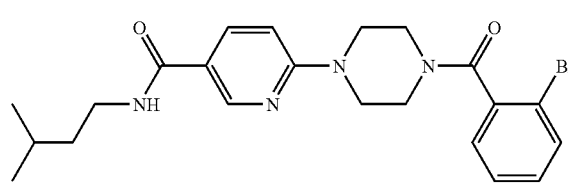
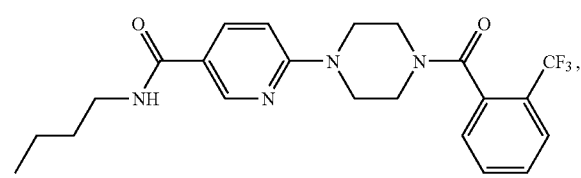
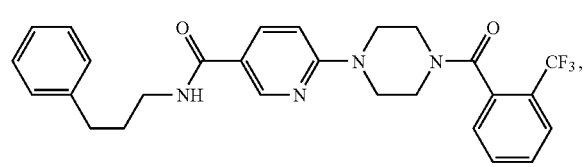
-continued
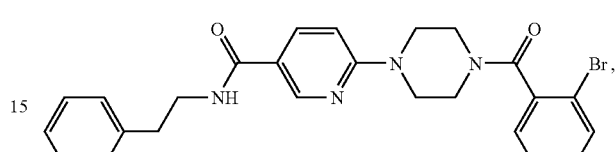

-continued
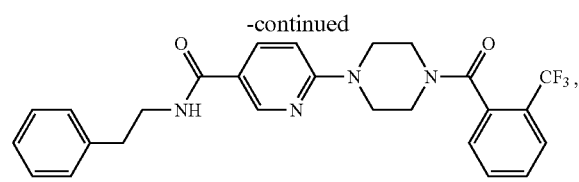
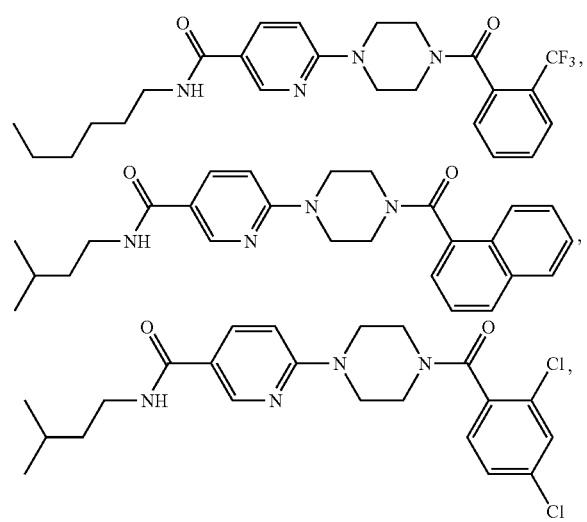
-continued
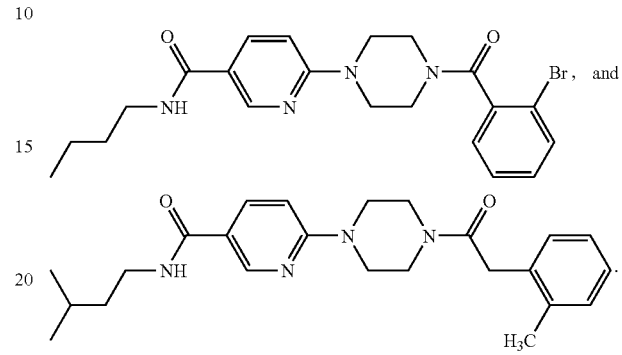
8. The method of claim 7 wherein the animal is a human.
* * * * *